United States Patent
Utay

(10) Patent No.: US 10,060,830 B2
(45) Date of Patent: Aug. 28, 2018

(54) IN-SITU SYSTEM AND METHOD OF DETERMINING COATING INTEGRITY OF TURBOMACHINERY COMPONENTS

(71) Applicant: UNITED TECHNOLOGIES CORPORATION, Farmington, CT (US)

(72) Inventor: Arthur W. Utay, South Windsor, CT (US)

(73) Assignee: UNITED TECHNOLOGIES CORPORATION, Farmington, CT (US)

(*) Notice: Subject to any disclaimer, the term of this patent is extended or adjusted under 35 U.S.C. 154(b) by 254 days.

(21) Appl. No.: 14/662,404

(22) Filed: Mar. 19, 2015

(65) Prior Publication Data

US 2015/0355055 A1     Dec. 10, 2015

Related U.S. Application Data

(60) Provisional application No. 62/009,389, filed on Jun. 9, 2014.

(51) Int. Cl.
    *G01M 15/14*      (2006.01)
    *G01N 21/35*      (2014.01)
    (Continued)

(52) U.S. Cl.
    CPC ............. *G01M 15/14* (2013.01); *F01D 17/02* (2013.01); *F01D 21/003* (2013.01); *G01N 21/35* (2013.01); *G01N 25/72* (2013.01); *F05D 2260/80* (2013.01)

(58) Field of Classification Search
    USPC .......................................... 73/112.01, 112.05
    See application file for complete search history.

(56) References Cited

U.S. PATENT DOCUMENTS

4,920,319 A * 4/1990 Viertl ...................... G01B 7/06
                                                               324/451
6,165,542 A * 12/2000 Jaworowski ......... G01N 27/025
                                                              427/10

(Continued)

FOREIGN PATENT DOCUMENTS

EP      1614864 A1      1/2006
GB      2397878 A      8/2004
JP      2002257764 A      9/2002

OTHER PUBLICATIONS

English Abstact for EP1614864A1—Jan. 11, 2006; 1 pg.
(Continued)

*Primary Examiner* — Eric S McCall
(74) *Attorney, Agent, or Firm* — Cantor Colburn LLP

(57) ABSTRACT

The present disclosure relates generally to a method of operating an inspection system, including a sensor and heating element operably coupled to a control module, to determine in-situ a coating integrity for a turbomachinery component within a turbomachinery system, the method comprising the steps of: placing the sensor and heating element at a distance from the desired turbomachinery component to be examine, operating the heating element for a predetermined amount of time, operating the sensor to detect an output from a surface of the turbomachinery component, and operating the control module to compare the output with at least one integrity parameter.

6 Claims, 4 Drawing Sheets

(51) Int. Cl.
*F01D 21/00* (2006.01)
*G01N 25/72* (2006.01)
*F01D 17/02* (2006.01)

(56) References Cited

U.S. PATENT DOCUMENTS

| | | | |
|---|---|---|---|
| 6,537,605 B1* | 3/2003 | Kirchner | C23C 4/00 118/302 |
| 2004/0179575 A1* | 9/2004 | Markham | G01J 5/0022 374/121 |
| 2005/0199832 A1 | 9/2005 | Twerdochlib | |
| 2011/0043820 A1* | 2/2011 | Sansom | G01B 11/0616 356/503 |
| 2014/0063227 A1* | 3/2014 | Baleine | G02B 23/2492 348/82 |
| 2014/0376589 A1* | 12/2014 | Karp | G01M 15/14 374/130 |

OTHER PUBLICATIONS

English Abstract for JP2002257764A—Sep. 11, 2002; 2 pgs.
EP Search Report for Application No. 15171117.3-1559; dated Oct. 23, 2015; 8 pgs.
Maffren T. et al.: "Influence of the Surface Roughness on Images Acquired by Flying Spot Active Thermography: Case of the High Pressure Turbine Blades"; 2013 IEEE International Instrumentation and Measurement Technology Conference; May 13, 2012, 4 pgs.

* cited by examiner

IN-SITU SYSTEM AND METHOD OF DETERMINING COATING INTEGRITY OF TURBOMACHINERY COMPONENTS

CROSS REFERENCE TO RELATED APPLICATIONS

The present application is related to, and claims the priority benefit of, U.S. Provisional Patent Application Ser. No. 62/009,389 filed Jun. 9, 2014, the contents of which are hereby incorporated in their entirety into the present disclosure.

TECHNICAL FIELD OF THE DISCLOSED EMBODIMENTS

The present disclosure is generally related to gas turbine engines and, more specifically, to an in-situ system and method of determining coating integrity of turbomachinery components.

BACKGROUND OF THE DISCLOSED EMBODIMENTS

Traditionally, turbomachinery, whether used in air, sea, or land-based applications, have provisions to visually inspect the equipment without removal of installed external equipment or teardown of the machine to access internal hardware. Typically plugs are removed on the external cases of the machine to allow the insertion of a fiber optic camera and light source, also known as a boroscope. Generally, the boroscope is a good tool for visual confirmation of the state of a blade, vane or other internal component of a turbomachine; however, it is limited in its ability to determine if a failure is imminent. Additionally, the visual examination is subjective, often resulting in false positives and negatives Turbomachinery internal components, especially those in hot locations of the machine, are often coated with additional materials to enhance their longevity and durability; however, determining the integrity of these coatings in-situ is difficult due to the limitations of a visual system. Improvements in determining the integrity of these coatings in-situ are therefore needed in the art.

SUMMARY OF THE DISCLOSED EMBODIMENTS

In one aspect, an inspection system for providing an in situ examination of a coating integrity of turbomachinery components within a turbomachinery system is provided. The system includes a control module, a sensor, and a heating element positioned adjacent to the sensor. The sensor and heating element are operably coupled to the control module via at least one cable.

In one embodiment, the control module includes a processor, a memory, a display, a power supply, and at least one input device, wherein the display, power supply, and at least one input device are operably coupled to the processor.

In at least one embodiment, the sensor includes an optical sensor. In one embodiment, the heating element includes an infrared heater. In one embodiment, the heating element is configured in the shape of an annulus. In one embodiment, the sensor is positioned substantially in the center of the annulus.

In one aspect, an in situ method of determining coating integrity of turbomachinery components within a turbomachinery system is provided. The method includes the step of inserting the sensor and heating element through an aperture of the turbomachinery system. The method also includes the step of placing the sensor and heating element at a distance from the desired turbomachinery component to be examined. In one embodiment, the sensor and the heating element are placed at a distance less than or equal to approximately 0.5 inch (12.7 mm) from the desired turbomachinery component to be examined.

The method further includes the step of operating the heating element for a predetermined amount of time. In one embodiment, the predetermined amount of time is determined by a type of coating applied to the turbomachinery component. In one embodiment, the predetermined amount of time is less than or equal to approximately 5 seconds.

The method further includes the step of operating the sensor to detect an output from a surface of the desired turbomachinery component. In one embodiment, the output includes a radiated output signature from the surface of the desired component. In one embodiment, the radiated output includes an infrared output. The method further includes the step of operating the control module to compare the output with at least one integrity parameter.

Other embodiments are also disclosed.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

DETAILED DESCRIPTION OF THE DISCLOSED EMBODIMENTS

Figure 1:
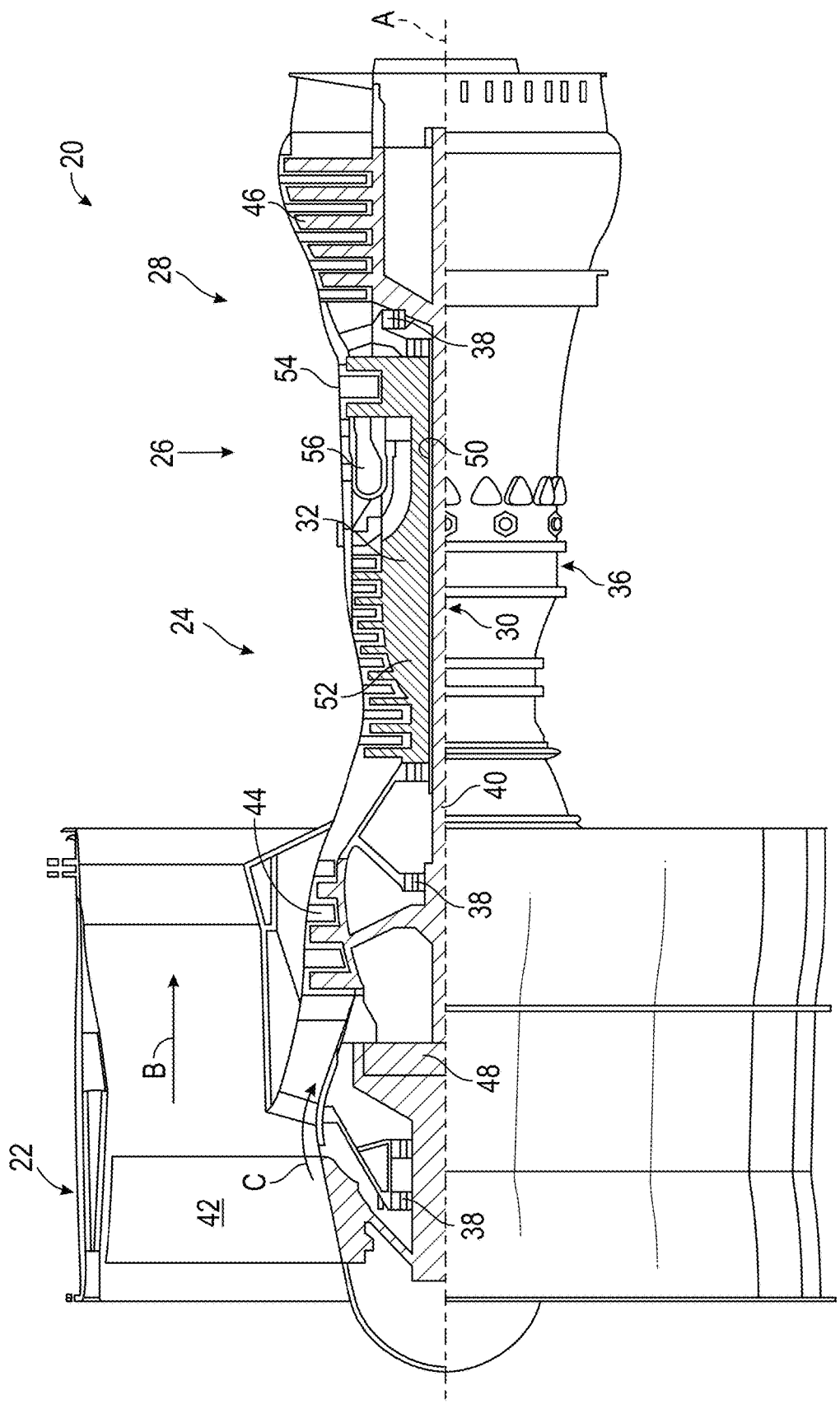
FIG. 1 is a schematic cross-sectional view of a gas turbine engine.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include an augmentor section (not shown) among other systems or features. The fan section 22 drives air along a bypass flow path B in a bypass duct, while the compressor section 24 drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The exemplary engine 20 generally includes a low speed spool 30 and a high speed spool 32 mounted for rotation about an engine central longitudinal axis A relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a low pressure compressor 44 and a low pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a high pressure compressor 52 and high pressure turbine 54. A combustor 56 is arranged in exemplary gas turbine 20 between the high pressure compressor 52 and the high pressure turbine 54. An engine static structure 36 is arranged generally between the high pressure turbine 54 and the low pressure turbine 46. The engine static structure 36 further supports bearing systems 38 in the turbine section 28. The inner shaft 40 and the outer shaft 50 are concentric and rotate via bearing systems 38 about the engine central longitudinal axis A which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, gear system 48 may be located aft of combustor section 26 or even aft of turbine section 28, and fan section 22 may be positioned forward or aft of the location of gear system 48.

The engine 20 in one example is a high-bypass geared aircraft engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present invention is applicable to other gas turbine engines including direct drive turbofans.

A significant amount of thrust is provided by the bypass flow B due to the high bypass ratio. The fan section 22 of the engine 20 is designed for a particular flight condition— typically cruise at about 0.8 Mach and about 35,000 feet (10,688 meters). The flight condition of 0.8 Mach and 35,000 ft., with the engine at its best fuel consumption—also known as "bucket cruise Thrust Specific Fuel Consumption ('TSFC')"—is the industry standard parameter of lbm of fuel being burned divided by lbf of thrust the engine produces at that minimum point. "Low fan pressure ratio" is the pressure ratio across the fan blade alone, without a Fan Exit Guide Vane ("FEGV") system. The low fan pressure ratio as disclosed herein according to one non-limiting embodiment is less than about 1.45. "Low corrected fan tip speed" is the actual fan tip speed in ft/sec divided by an industry standard temperature correction of $[(Tram\ ^\circ R)/(518.7^\circ R)]^{0.5}$. The "Low corrected fan tip speed" as disclosed herein according to one non-limiting embodiment is less than about 1150 ft/second (350.5 m/sec).

Figure 2:
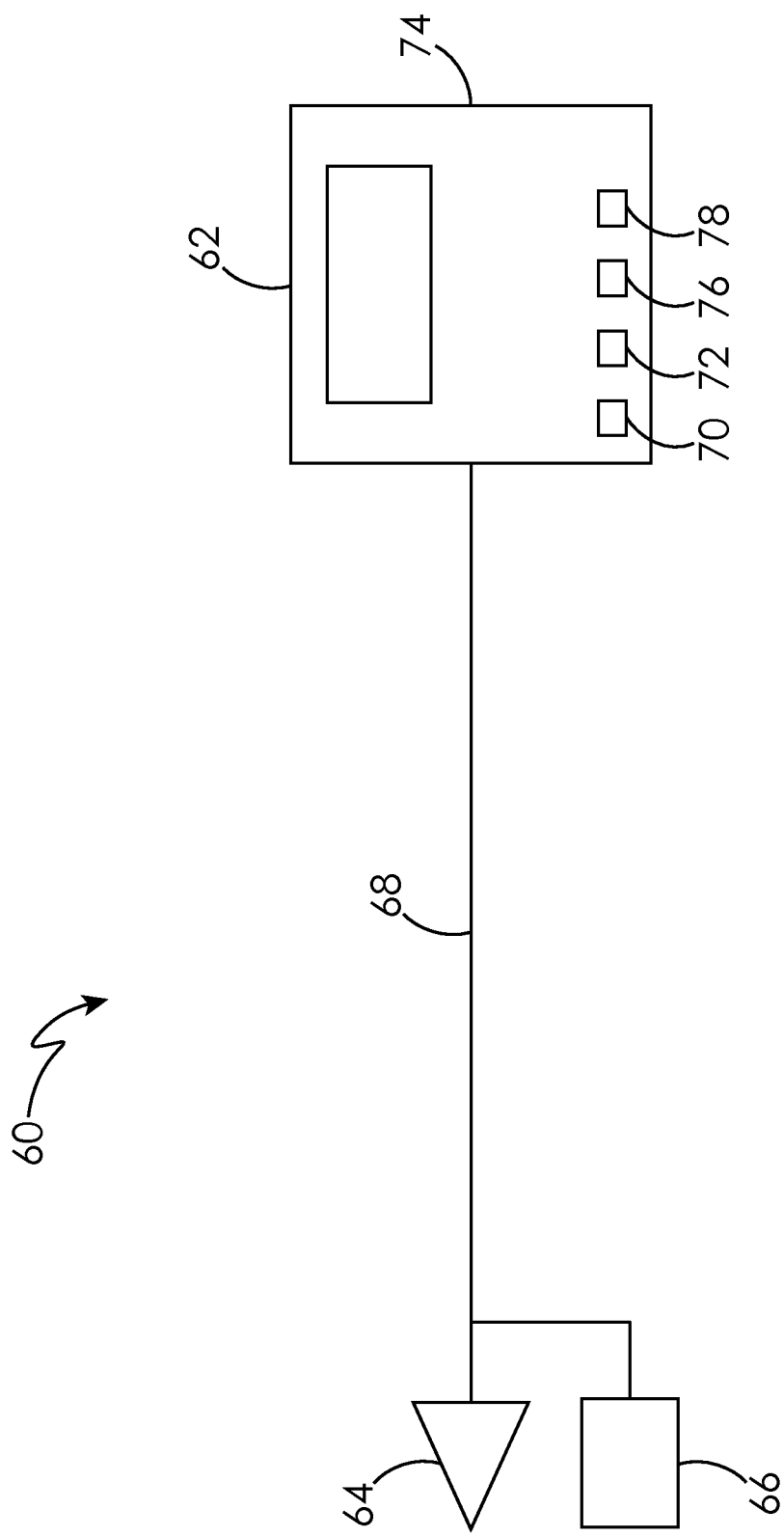
FIG. 2 is a schematic diagram of an inspection system in an embodiment.

FIG. 2 illustrates an inspection system 60 for providing an in situ examination of a coating integrity of turbomachinery components within a turbomachinery system (e.g. gas turbine engine 20). The system 60 includes a control module 62, a sensor 64, and a heating element 66 positioned adjacent to the sensor 64.

The sensor 64 and heating element 66 are operably coupled to the control module 62 via at least one cable 68. The at least one cable 68 is configured to transmit data from the sensor 64 to the control module 62. The at least one cable 68 is also configured to supply power from the control module 62 to the sensor 64 and the heating element 66. It will be appreciated that the at least one cable 68 may be inserted into a flexible conduit (not shown) to protect the at least one cable 68 from damage.

In one embodiment, the control module 62 includes a processor 70, a memory 72, a display 74, a power supply 76, and at least one input device 78, wherein the display 74, power supply 76, and at least one input device 78 are operably coupled to the processor 70. It will be appreciated that the display 74 includes a liquid crystal display to name one non-limiting example. It will also be appreciated that the at last one input device 78 includes a button, switch, or toggle-switch to name a few non-limiting examples.

In at least one embodiment, the sensor 64 includes an optical sensor. In one embodiment, the heating element 66 includes an infrared heater. In one embodiment, the heating element 66 is configured in the shape of an annulus. In one embodiment, the sensor 64 is positioned substantially in the center of the annulus.

Figure 3:
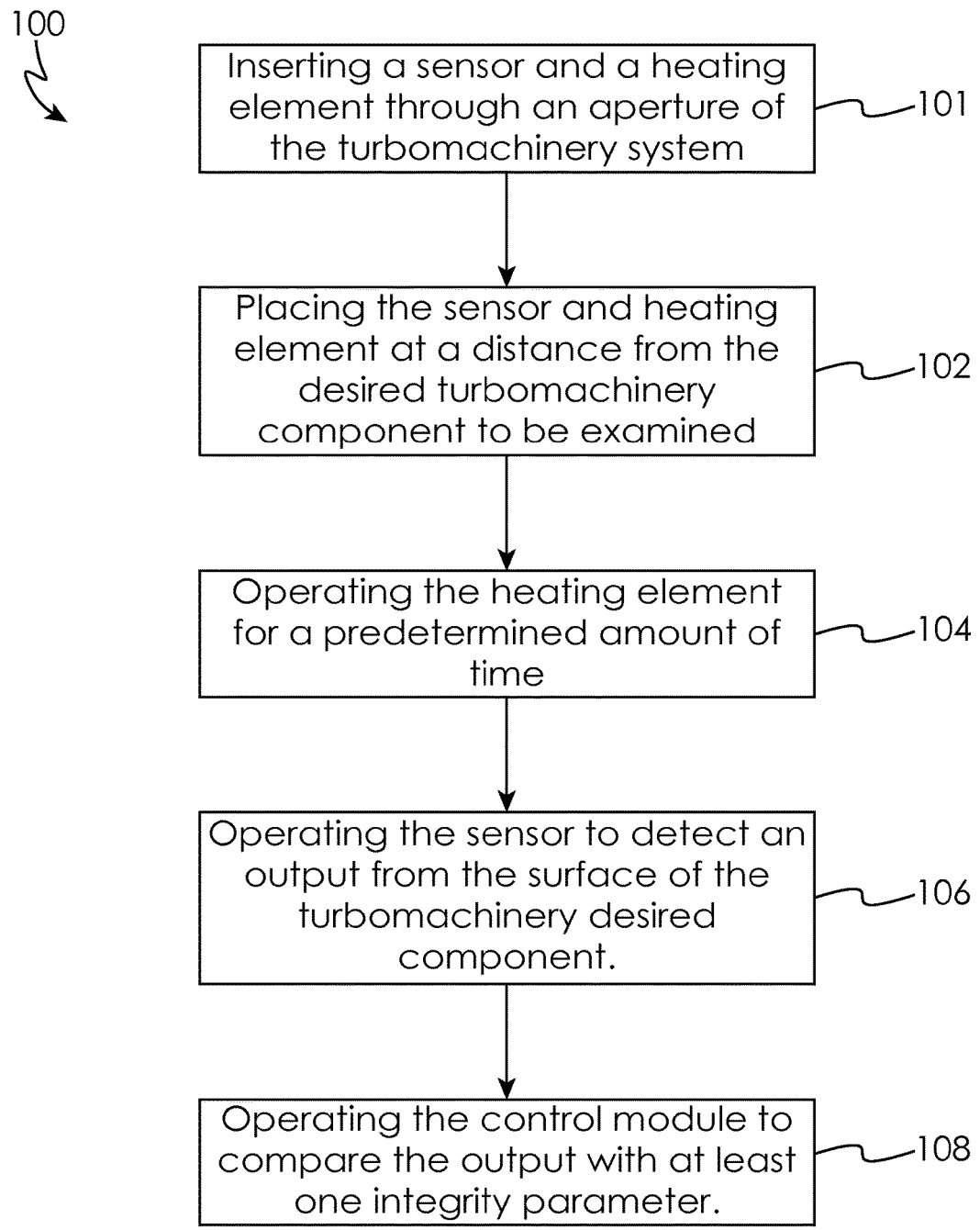
FIG. 3 is a cross-sectional view of a surface of a turbomachinery component in an embodiment.
Figure 4:
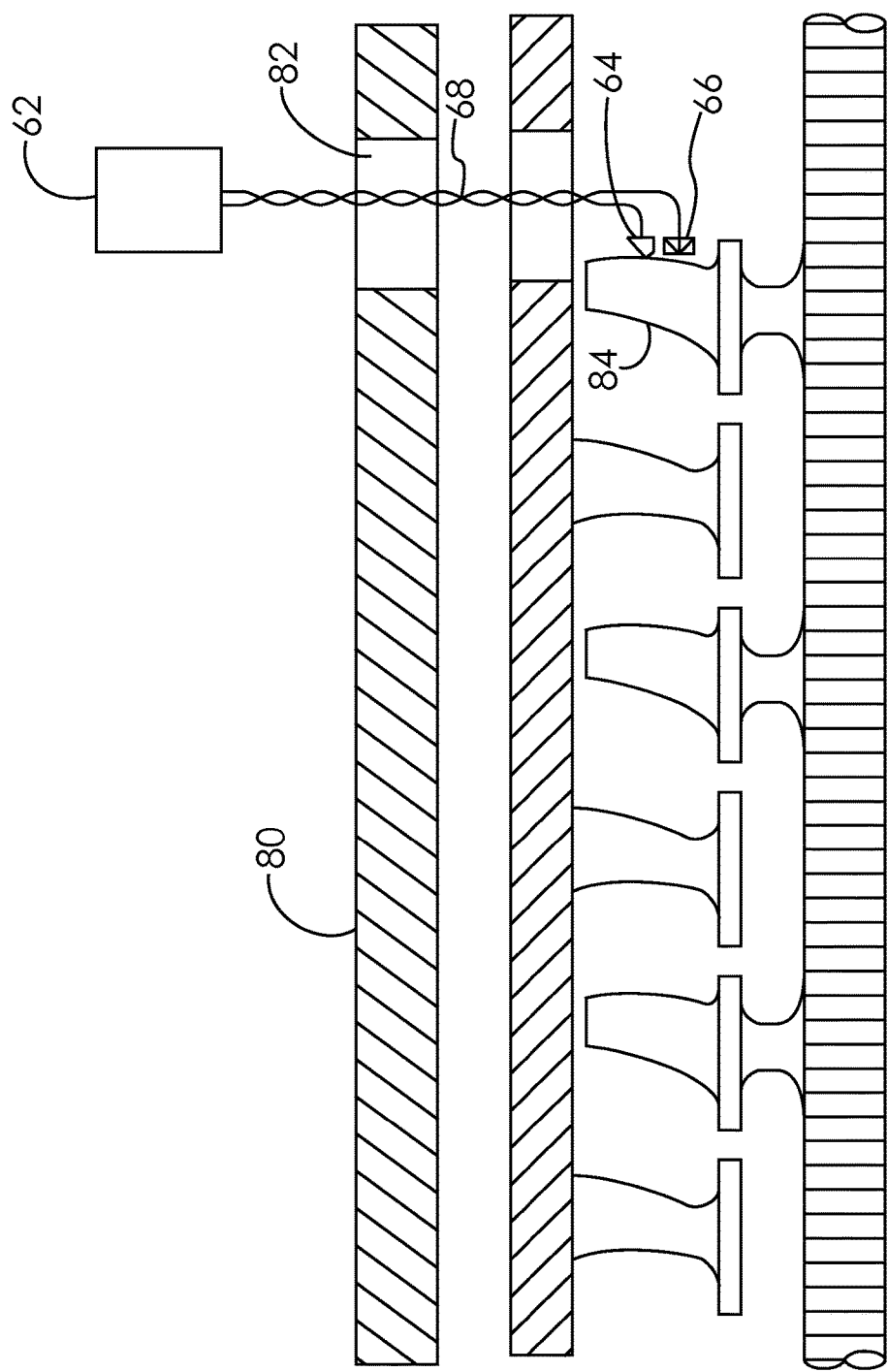
FIG. 4 is a schematic flow diagram of an in-situ method for determining coating integrity of a turbomachinery component.

FIG. 3 illustrates an in situ method 100 of determining coating integrity of turbomachinery components within a turbomachinery system utilizing the inspection system 60 as described herein, the method includes step 102 of placing the sensor 64 and heating element 66 at a distance from the desired turbomachinery component to be examined. In one embodiment, step 102 further includes step 101 of inserting the sensor 64 and heating element 66 through an aperture of the turbomachinery system. In one embodiment the sensor 64 and the heating element 66 are placed at a distance less than or equal to approximately 0.5 inch (12.7 mm) from the desired turbomachinery component to be examined. For example, as shown in FIG. 4, the sensor 64, heating element 66, and at least one cable 68 are inserted through the aperture 82 of turbomachinery system 80 and placed at a distance less than or equal to approximately 0.5 inch (12.7 mm) from turbomachinery component 84. It will be appreciated that the turbomachinery component 84 may include a blade, vane, air seal, or any turbomachinery component 84 containing a coating thereon to name a few non-limiting examples.

The method further includes step 104 of operating the heating element 66 for a predetermined amount of time. In one embodiment, the predetermined amount of time is determined by a type of coating applied to the turbomachinery component 84. In one embodiment, the predetermined amount of time is less than or equal to approximately 5 seconds. It will be appreciated that the predetermined amount of time may be greater than 5 seconds. For example, if the coating on the desired component is 0.030 inch (0.762 mm) thick, the predetermined amount of time is equal to approximately 3 seconds. Operating the heating element 66 includes supplying power to the heating element 66 from the power supply 76, within the control module 62, via the at least one cable 68.

The method further includes step 106 of operating the sensor 64 to detect an output from a surface of the desired turbomachinery component 84. In one embodiment, the output includes a radiated output signature from the surface of the desired component. In one embodiment, the radiated output includes an infrared output. For example, heat is transferred from the heating element 66 to the surface of the turbomachinery component 84. As the temperature increases on the surface of the turbomachinery component 84, the coating disposed thereon emits a radiated output signature based on its composition.

The method further includes step 108 of operating the control module 78 to compare the output with at least one integrity parameter. For example, the infrared output will be of varying shades from white to black. An example of an integrity parameter may be to compare the shade from the part against a standard coded into the control module. It will be appreciated that additional integrity parameters may be used. For example, after the sensor 64 detects the radiated output signature from the surface of the turbomachinery component 84, the sensor 64 transmits the radiated output signature to the control module 62 via the at least one second cable 68. The at least one integrity parameter may be pre-loaded into the memory 72 of the control module 62. The processor 70 executes software stored in the memory 72 to compare the radiated output signature to the at least one integrity parameter. Based on the comparison of the radiated output signature to the at least one integrity parameter, a user may determine the integrity of the coating of the desired turbomachinery component 84. For example, a user may be able to determine a coating thickness, areas of delamination, and/or whether any surface cracks are present.

It will be appreciated that the inspection system 60 may be utilized to operate the sensor 64 and heating element 66 to determine if coating failures have occurred or are imminent without removal of the turbomachinery component 84 from the turbomachinery system.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method of operating a system to determine in-situ a coating integrity for a turbomachinery component within a turbomachinery system,
    the system including:
        a control module including a processor operably coupled within the control module to a memory, a display, a power supply, and at least one input device,
        a sensor that is an optical sensor, the sensor being operatively coupled to the control module by a first cable, the first cable providing power to the sensor and transmitting data from the sensor to the control module, and
        a heating element that is an infrared heating element, the heating element being operably coupled to the control module by a second cable, the second cable providing power to the heating element,
        the sensor and heating element being movable relative to the control module,
    the method comprising the control module performing steps of:
    (a) moving the sensor and heating element relative to the control module and the turbomachinery system,
    (b) inserting the sensor and heating element through an aperture of the turbomachinery system for in situ examination of the coating integrity for the turbomachinery component within the turbomachinery system,
    (b) positioning the sensor and heating element so that the sensor and heating element proximate each other and the sensor and heating element are proximate the turbomachinery component,
    (c) operating the heating element for a predetermined amount of time,
    (d) operating the sensor to detect an output from a surface of the desired turbomachinery component, the output being a radiated output signature, and
    (e) comparing the output detected from the sensor with at least one integrity parameter.

2. The method of claim 1 wherein the sensor and heating element are spaced from the turbomachinery component by a distance that is less than or equal to approximately 0.5 inch (12.7 mm).

3. The method of claim 1, wherein the predetermined amount of time is determined based on a type of coating applied to the turbomachinery component.

4. The method of claim 3, wherein the predetermined amount of time is less than or equal to approximately 5 seconds.

5. An inspection system for determining in-situ a coating integrity for a turbomachinery component within a turbomachinery system comprising:
    a control module including a processor operably coupled within the control module to a memory, a display, a power supply, and at least one input device,
    a sensor that is an optical sensor, the sensor being operatively coupled to the control module by a first cable, the first cable providing power to the sensor and transmitting data from the sensor to the control module, and
    a heating element that is an infrared heating element, the heating element being operably coupled to the control module by a second cable, the second cable providing power to the heating element,
    the sensor and heating element being movable relative to the control module,
    wherein the control module is configured to:
    (a) move the sensor and heating element relative to the control module and turbomachinery system,
    (b) insert the sensor and heating element through an aperture of the turbomachinery system for in situ examination of the coating integrity for the turbomachinery component within the turbomachinery system,
    (c) position the sensor and heating element so that the sensor and heating element proximate each other and the sensor and heating element are proximate the turbomachinery component, (c) operate the heating element for a predetermined amount of time,
(d) operate the sensor to detect an output from a surface of the turbomachinery component, the output being a radiated output signature, and
(e) compare the output detected from the sensor with at least one integrity parameter.

6. The inspection system of claim 5, wherein the heating element is configured in the shape of an annulus.

\* \* \* \* \*